United States Patent

Sakakibara et al.

[11] 4,288,634
[45] Sep. 8, 1981

[54] NOVEL RHODIUM COMPOUNDS AND PROCESS FOR PRODUCING THE SAME

[75] Inventors: Tadamori Sakakibara; Yoshihisa Matsushima; Yukio Nagashima; Nobukazu Okamoto; Katsumi Kaneko, all of Ooi; Yohio Ishii, Nagoya; Shozo Wada, Zushi, all of Japan

[73] Assignee: Toa Nenryo Kogyo Kabushiki Kaisha, Tokyo, Japan

[21] Appl. No.: 73,664

[22] Filed: Sep. 7, 1979

[30] Foreign Application Priority Data

Apr. 10, 1978 [JP] Japan .................................. 53/121456
Apr. 10, 1978 [JP] Japan .................................. 53/121457

[51] Int. Cl.³ .......................................... C07C 45/50
[52] U.S. Cl. ................................................... 568/454
[58] Field of Search ......................................... 568/454

[56] References Cited

U.S. PATENT DOCUMENTS

| | | | |
|---|---|---|---|
| 3,168,553 | 2/1965 | Slaugh | 260/604 HF |
| 3,487,112 | 6/1969 | Paulik et al. | 260/604 HF |
| 3,527,809 | 9/1970 | Pruett et al. | 260/604 HF |
| 3,821,311 | 6/1974 | Hughes | 260/604 HF |
| 3,857,900 | 12/1974 | Wilkinson | 252/431 |
| 3,954,877 | 5/1976 | Gipson | 260/604 HF |
| 4,052,461 | 10/1977 | Tinker | 260/604 HF |
| 4,148,830 | 4/1979 | Pruett | 260/604 HF |

FOREIGN PATENT DOCUMENTS 1298331 11/1972 United Kingdom ......... 260/604 HF
1357735 6/1974 United Kingdom ......... 260/604 HF
1440413 6/1976 United Kingdom ......... 260/604 HF

OTHER PUBLICATIONS

Catalyst Reviews, vol. 6 (1), pp. 66–83, (1972).
J. of Synthetic Organic Chemistry (Japan), vol. 35, (8), pp. 683–688, (1977).
Hydrocarbon Processing, vol. 6, pp. 83–91, (1975).
Chem. Eng. vol. 26, p. 109, Dec. 5, 1977.

Primary Examiner—Werren B. Lone
Attorney, Agent, or Firm—Rebecca Yablonsky

[57] ABSTRACT

This invention relates to rhodium compounds having the general formula:

$$HRh(CO)(XR_3)_n(YR'_3)_{3-n}$$

wherein X is phosphorus, arsenic or antimony; Y is arsenic or antimony when X is phosphorus, Y is phosphorus or antimony when X is arsenic, or Y is phosphorus, arsenic or antimony when X is antimony; R and R' are aryl groups; and n is an integer of 1 or 2. Further, it relates to a process for the preparation of aldehydes by the hydroformylation of olefins in the presence of a rhodium catalyst, and more particularly for the production of aldehydes by the reaction of olefins such as propylene with carbon monoxide and hydrogen in the presence of $HRh(CO)(PPh_3)_2(AsPh_3)$/excess $PPh_3$ and $AsPh_3$ or $HRh(CO)(PPh_3)(AsPh_3)_2$/excess $PPh_3$ and $AsPh_3$.

5 Claims, 2 Drawing Figures

Sum of the Pauling electro-negativities (Xp)

Sum of the Pauling electro-negativities (Xp)

Sum of the Pauling electro-negativities (Xp)

NOVEL RHODIUM COMPOUNDS AND PROCESS FOR PRODUCING THE SAME

BACKGROUND OF THE INVENTION

1. Field of the Invention

This invention relates to new rhodium compounds and a process for producing the same. More particularly, it is concerned with new rhodium compounds having a structure isoelectronic to $HRh(CO)(PPh_3)_3$ and a process for the selective production of the same. Further, it relates to use of such products as catalysts in the oxo process.

2. Description of the Prior Art

Carbonyl tris (triphenylphosphine) rhodium hydride is known as a catalyst having activity in various chemical reactions for organic syntheses, for example, in hydroformylation. (Japanese Patent Publication No. 10730/1970 equivalent to U.S. Pat. No. 3,527,809). See also U.S. Pat. No. 3,821,311 and Canadian Pat. No. 992,101. As rhodium compounds having a structure isoelectronic thereto are known carbonyl tris(triphenylphosphite) rhodium hydride $HRh(CO)(P(OPh)_3)_3$ (British Pat. No. 1338225), carbonyl tris(triphenylarsine) rhodium hydride $HRh(CO)(AsPh_3)_3$ and carbonyl tris (triphenylarsite) rhodium hydride $HRh(CO)(As(OPh)_3)_3$ (British Pat. No. 1357735). As to producing these compounds, some processes are known. In the case of $HRh(CO)(PPh_3)_3$, for example, there have been proposed (1) a process comprising reacting rhodium trichloride. trihydrate, excess triphenylphosphine, an aqueous solution of formaldehyde and sodium borohydride in boiling ethanol (Journal of the Chemical Society (A), 1968, page 2660), (2) a process comprising reacting carbonyl bis(triphenylphosphine) rhodium chloride, excess triphenylphosphine and sodium borohydride in boiling ethanol (ibid) and (3) a process comprising contacting carbonyl bis(triphenylphosphine) rhodium chloride and excess triphenylphosphine with synthesis gas (mixture of $H_2$ and CO) at a temperature of at least 55° C. under a pressure of at least 10 atm. (Japanese Patent Publication No. 17572/1978).

However, carbonyl tris(triphenylstibine) rhodium hydride $HRh(CO)(SbPh_3)_3$ having a structure isoelectronic to the above described rhodium compounds has not been synthesized and isolated. Moreover, as is evident from the foregoing description, all the rhodium compounds having the above described known structures contain respectively a single kind of ligand and those containing different kinds of mixed ligands, for example, phosphines and arsines in the same molecule, are not known, although some monovalent rhodium compounds containing mixed ligands in the same molecule are known, for example, carbonyl triphenylphosphine triphenylarsine rhodium chloride $RhCl(CO)(PPh_3)(AsPh_3)$ (Journal of Organometallic Chemistry, Vol. 43, No. 2, 1972, page 425), carbonyl triphenylphosphine triphenylstibine rhodium chloride $RhCl(CO)(PPh_3)(SbPh_3)$ (ibid), carbonyl triphenylarsine triphenylstibine rhodium chloride $RhCl(CO)(AsPh_3)(SbPh_3)$ (ibid) and carbonyl (diethylphenylphosphine) (tri-o-toluylstibine) rhodium chloride $RhCl(CO)(PPhEt_2)(Sb(o—CH_2C_6H_4)_3)$ (Inorganic Chemistry, Vol. 15, No. 13, 1976, page 646). See also J. Chem. Soc. D1970, (17), 1077–8 (England); Inorg. Nucl. Chem. Lett. 1971, 7(9)877–9 (England); J. Chem. Soc. Dalton Trans. 1972 (19) 2161–9 (England) and U.S. Pat. No. 3,459,780. As a method for synthesizing these compounds, it has been proposed to add to a binuclear rhodium compound $(RhCl(CO)L)_2$ wherein L is triphenylphosphine, triphenylarsine or triphenylstibine in warm benzene an ether solution of 2 mols (equimolar amount) of L' being triphenylphosphine, triphenylarsine or triphenylstibine but not the same as L (Journal of Organometallic Chemistry, Vol. 43, No. 2, 1972, page 425).

Other references of lesser interest, noted because they concern rhodium-containing compounds, are U.S. Pat. Nos. 3,939,188 and 3,946,082, which relate to compounds containing reduced, zero valent rhodium and U.S. Pat. No. 4,052,461 which relates to ionic rhodium compounds but not the hydrides which are nonionic.

However, mixed ligands-containing rhodium compounds having a structure isoelectronic to $HRh(CO)(PPh_3)_3$ or three stibines-coordinated rhodium compounds cannot be obtained, or mixtures of various rhodium compounds are only obtained, by the above described method or other known methods and it is very difficult to isolate such compounds in a pure form.

Rhodium-phosphine type or rhodium-phosphite type complexes are known as catalysts for the hydroformylation of olefins. The stability of a rhodium catalyst is increased by modification with phosphine, arsine, or stibine, which permits practicing the oxo reaction at a rather low pressure.

According to Japanese Pat. No. 903,326, straight chain-rich aldehydes are prepared at a low total pressure with a low partial pressure of carbon monoxide and a high partial pressure of hydrogen in the presence of a rhodium triarylphosphine catalyst and a triarylphosphine ligand in a large exess to the rhodium. However, this method has the disadvantage that the hydroformylation reaction rate of an olefin is markedly decreased because of using a ligand in a large excess to rhodium, and a considerable quantity of a paraffin is formed by the hydrogenation of the olefin ("Hydrocarbon Processing" (4) 112 (1970)) due to the reaction at a low total pressure with a low partial pressure of carbon monoxide and a high partial pressure of hydrogen.

Rhodium catalysts in combination with arsines or stibines instead of phosphines have been proposed, but the studies thereof have not been made so intensively because of their lower activity compared with tertiary phosphine-rhodium catalysts.

SUMMARY OF THE INVENTION

Applicants have made various efforts to obtain new rhodium compounds having a structure isoelectronic to $HRh(CO)(PPh_3)_3$ and, as a result, have succeeded in obtaining new rhodium compounds represented by the following general formula in high yield and in a pure form, thus accomplishing the present invention. It is estimated that in the new compounds the rhodium is mono-valent. This invention further relates to a process for the production of aldehydes by the hydroformylation of olefins and more particularly, it is concerned with an improved process for producing aldehydes by reacting olefins, carbon monoxide and hydrogen in the presence of rhodium-containing complex compound catalysts and free ligands. That is to say, the gist of the present invention consists in novel rhodium compounds represented by the general formula, $$Rh(CO)(XR_3)_n(YR'_3)_{3-n} \tag{A}$$

wherein X is phosphorus, arsenic or antimony; Y is arsenic or antimony when X is phosphorus, Y is phosphorus or antimony when X is arsenic or Y is phosphorus, arsenic or antimony when X is antimony; R and R' are aryl groups, which may be the same or different; and n is an integer of 1 or 2, and a process for their production.

Further, applicants have made studies of hydroformylation using a catalyst system comprising rhodium and mixed ligands of tertiary organo phosphorus ligands and tertiary organo arsenic ligands in combination and have found that, surprisingly, when hydroformylation of an olefin is carried out with this catalyst system in the presence of excess mixed ligands, the reaction rate is remarkably improved, the quantity of paraffin formed by the hydrogenation of the olefin is decreased and, in addition, the selectivity to normal chain aldehyde is kept similar or improved in comparison with carrying out the reaction in the presence of a tertiary organo phosphorus rhodium catalyst and excess tertiary organo phosphorus ligand. Also, the catalyst can be re-used with maintenance of its activity after separating the prepared aldehyde by suitable means such as distillation and the like.

Therefore, the present invention provides a commercially valuable process whereby hydroformylation of an olefin is improved using a rhodium complex containing both a tertiary organo phosphorus compound and tertiary organo arsenic compound in a rhodium complex $HRh(CO)(ligand)_3$ which is an active species for the hydroformylation in the presence of an excess quantity of mixed ligands of a tertiary organo phosphorus compound and tertiary organo arsenic compound.

That is to say, the present invention relates to a process for producing aldehydes by reacting an olefin with carbon monoxide and hydrogen, the aldehydes having one more carbon atom than the olefin, which comprises carrying out the reaction using a rhodium catalyst containing a tertiary organo phosphorus and tertiary organo arsenic represented by the general formula $X'R''_3$ (wherein $X'$ represents phosphorus or arsenic and $R''$ represents an organic group, in particular, alkyl, cycloalkyl, aryl or aralkyl group, which may be same or different) and carbon monoxide in the presence of free mixed ligands comprising a tertiary organo phosphorus and tertiary organo arsenic represented by the general formula $X'R''_3$ (wherein $R''$ has the same meaning as just described and may be same as or different from those contained in the above described rhodium catalyst) in excess of the quantity required for coordination to the rhodium atom.

DETAILED DESCRIPTION

The novel rhodium compounds included in the above described general formula (A) are classified into the following seven groups:

(I) $HRh(CO)(PR_3)_2(AsR'_3)$
(II) $HRh(CO)(PR_3)(AsR'_3)_2$
(III) $HRh(CO)(PR_3)_2(SbR'_3)$
(IV) $HRh(CO)(PR_3)(SbR'_3)_2$
(V) $HRh(CO)(AsR_3)_2(SbR'_3)$
(VI) $HRh(CO)(AsR_3)(SbR'_3)_2$
(VII) $HRh(CO)(SbR_3)_3$ (R and R' have the same meanings as described above.)

Figure 1:
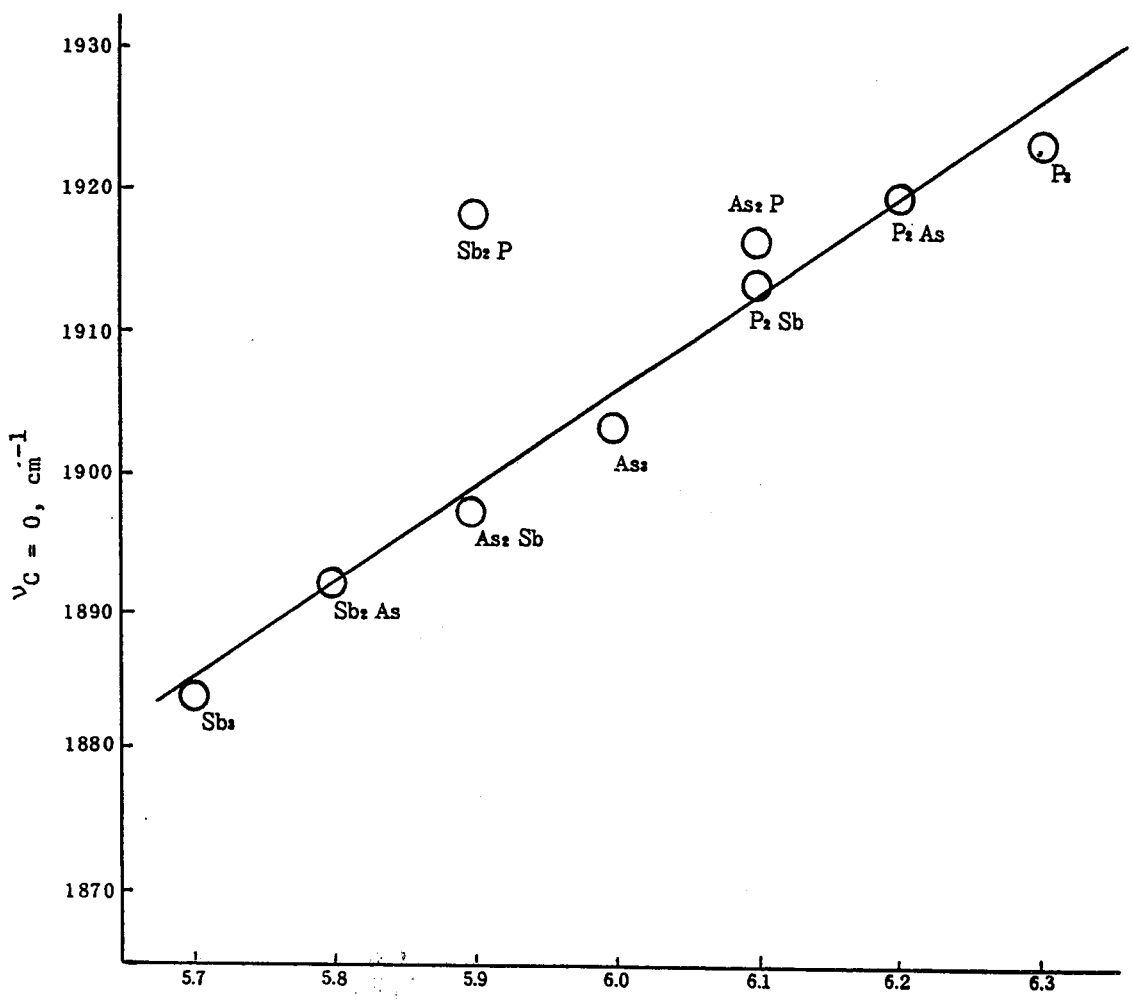
FIGS. 1 and 2 are graphs showing the relationships between the sum of the Pauling electro-negativities and $\nu_{C-O}$ and $\nu_{Rh-H}$ respectively of compounds of this invention.
Figure 2:
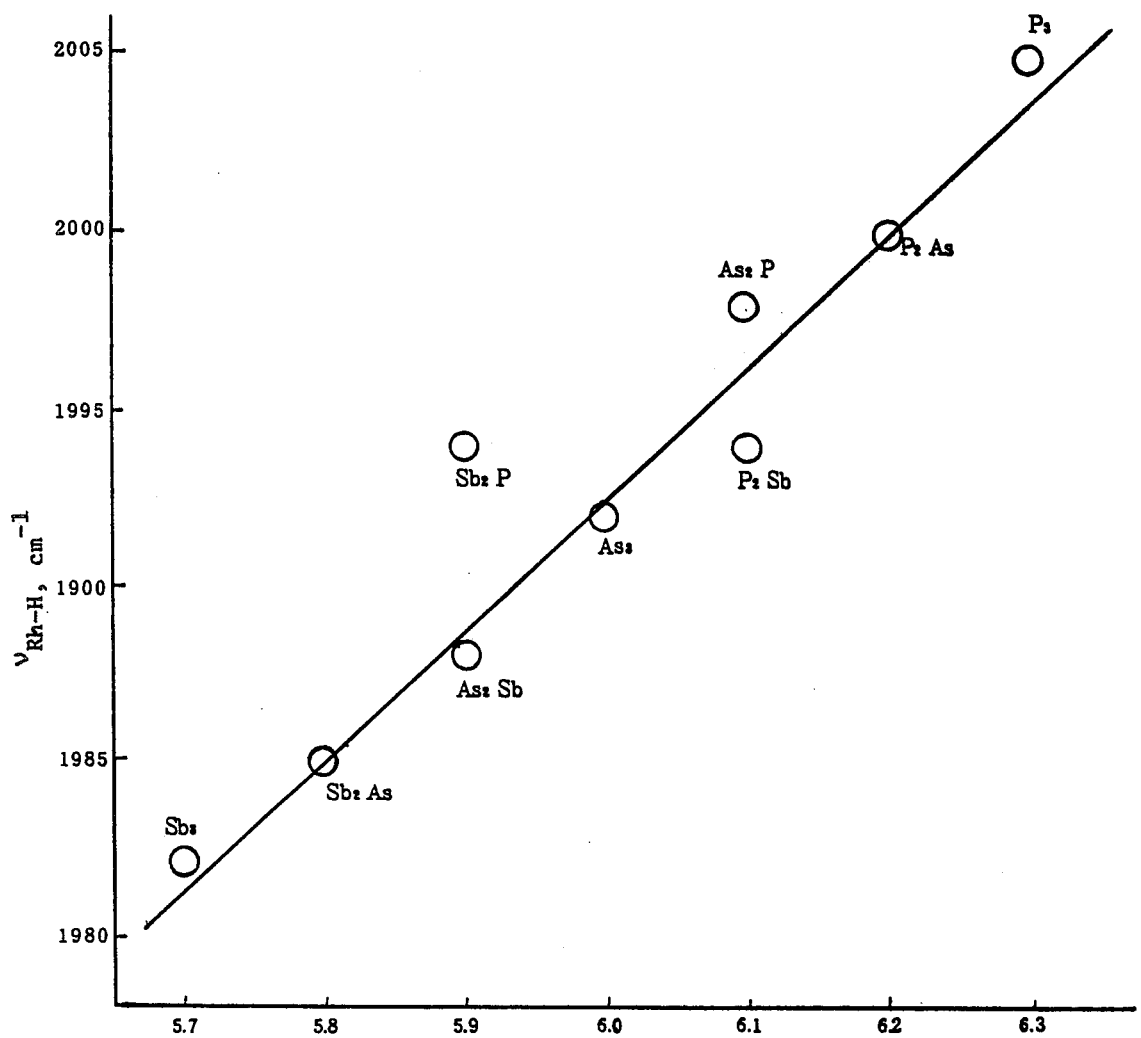

Useful examples of these compounds, in particular where R and R' are the same and are phenyl groups, are as follows:

(1) Carbonyl bis(triphenylphosphine) triphenylarsine rhodium hydride $HRh(CO)(PPh_3)_2(AsPh_3)$ (2) Carbonyl bis(triphenylphosphine) triphenylstibine rhodium hydride $HRh(CO)(SbPh_3)(PPh_3)_2$ (3) Carbonyl bis(triphenylarsine) triphenylphosphine rhodium hydride $HRh(CO)(PPh_3)(AsPh_3)_2$ (4) Carbonyl bis(triphenylarsine) triphenylstibine rhodium hydride $HRh(CO)(SbPh_3)(AsPh_3)_2$ (5) Carbonyl bis(triphenylstibine) triphenylphosphine rhodium hydride $HRh(CO)(PPh_3)(SbPh_3)_2$ (6) Carbonyl bis(triphenylstibine) triphenylarsine rhodium hydride $HRh(CO)(AsPh_3)(SbPh_3)_2$ (7) Carbonyl tris(triphenylstibine) rhodium hydride $HRh(CO)(SbPh_3)_3$ The structural formulas of these seven kinds of the novel compounds were confirmed by an IR spectrophotometer and elementary analysis, results shown in Tables 1 and 2 being obtained. As can be seen from Table 1, the IR data of the compounds of the present invention show that the absorption based on the stretching frequency of Rh-H ($\nu_{Rh-H}$) appears near 2000 cm$^{-1}$, the absorption based on the stretching frequency of C=O ($\nu_{C=O}$) appears near 1900 cm$^{-1}$ and the absorption zones are substantially similar to those of $\nu_{Rh-H}$ and $\nu_{C=O}$ of the known compounds $HRh(CO)(PPh_3)_3$ and $HRh(CO)(AsPh_3)_3$. In addition, there is a linear relationship between the sum of the Pauling electronegativities of the elements and $\nu_{C=O}$ or $\nu_{Rh-H}$ in these compounds, respectively as shown in FIG. 1 and FIG. 2 (In FIG. 1 and FIG. 2, $P_3 = HRh(CO)(PPh_3)_3$*, $P_2As = HRh(CO)(PPh_3)_2(AsPh_3)$, $As_2P = HRh(CO)(AsPh_3)_2(PPh_3)$, $P_2Sb = HRh(CO)(PPh_3)_2(SbPh_3)$, $As_3 = HRh(CO)(AsPh_3)_3$*, $Sb_2P = HRh(CO)(SbPh_3)_2(PPh_3)$, $As_2Sb = HRh(CO)(AsPh_3)_2(SbPh_3)$, $Sb_2As = HRh(CO)(SbPh_3)_2(AsPh_3)$, $Sb_3 = HRh(CO)(SbPh_3)_3$, mark *=known compound). As apparent from Table 2, the found values in the elementary analysis of these compounds coincide exactly with calculated ones and thus it is confirmed that the compounds of the present invention have the designated general formula.

For the production of these compounds, the various known methods or the method comprising reacting a monovalent rhodium compound containing mixed ligands and excess ligands in the presence of sodium borohydride or hydrazine in boiling ethanol has the disadvantage set forth above that starting materials only are recovered, starting materials themselves are decomposed or a mixture of various rhodium compounds is only obtained and isolation of the desired compound is very difficult.

However, applicants have found that these compounds can be obtained in high selectivity and high yield by first contacting a compound of the general formula $RhZ(CO)(XR_3)_2$ in which Z is a halide anion selected from chloride, bromide and iodide, and X and R have the meanings given with a compound of the general formula $YR'_3$ in which Y and R' have the meanings given in a selected amount depending on the above compound, in a solvent, then adding a reducing agent carefully at a relatively low temperature and thereby reacting them.

The molar ratio of YR'$_3$ to RhZ(CO)(XR$_3$)$_2$ used in the present invention, depends on the properties of the starting materials and the rhodium compound to be formed. In order to obtain the desired compound in a pure form, it is desirable to use YR'$_3$ in at least the equimolar amount. When using YR'$_3$ in too large an excess, however, the desired compound is obtained in a mixed state with the ligand, as a result of which a number of washings with a solvent will be needed. This is disadvantageous economically and, accordingly, the molar ratio is preferably 1.0 to 10.

Addition of reducing agents before the contacting of RhZ(CO)(XR$_3$)$_2$ with YR'$_3$ is not desirable because various reactions are thereby caused to take place resulting in deterioration of the reactants. Therefore it is very important to contact the two, suitably by the use of solvents, before adding a reducing agent.

In the present invention, any solvents may be used which are capable of dissolving, at least partly, RhZ(CO)(XR$_3$)$_2$ and/or YR'$_3$ but do not react with them. Illustrative of such solvents are aromatic hydrocarbons such as benzene, toluene and lower alcohols such as methanol, ethanol, propanol, isopropanol.

Preferred solvents are lower alcohols, and above all, ethanol may be used in view of advantages in practical operation.

The temperature of contact of RhZ(CO)(XR$_3$)$_2$ and YR'$_3$ can be varied widely within the range in which they are not decomposed, but preferably ranges from room temperature to about 100° C., most preferably from about 40° to about 80° C.

Most useful examples of the reducing agent used in the present invention are alkali metal borohydrides such as sodium borohydride, NaBH$_4$, potassium borohydride, KBH$_4$, and lithium borohydride; boranes such as borane, BH$_3$, diborane, B$_2$H$_6$, and tetraborane, B$_4$H$_{10}$; and hydrides of Group IIIA elements such as aluminum, for example, lithium aluminum hydride. Sodium borohydride is preferred because of its cheapness and ease of handling.

When the reducing agent is added at a high temperature after both the reactants are contacted, the heat of reaction sometimes brings about unfavorable side reactions and, therefore, it is desirable to cool to a temperature lower than room temperature, preferably around 0° C., prior to addition of the reducing agent.

The quantity of reducing agent used in the present invention is not particularly limited since no side reaction occurs even if a large quantity of the reducing agent is added, but, in general, a proportion of 5 to 50 mols to 1 mol of RhZ(CO)(XR$_3$)$_2$ is sufficient. The reducing agent can be added as a solid to the foregoing mixed solution, but is preferably added in the form of a solution in a lower alcohol, etc.

In order to prevent the rapid generation of heat due to the reducing reaction, it is desirable to add the reducing agent gradually while controlling the temperature and stirring the solution adequately. After the reducing agent has been added, cooling may be stopped and the mixture allowed to return to room temperature. The stirring is preferably continued even after the reducing agent is added. This period of time is not particularly limited but usually 1 to 3 hours is sufficient.

When these procedures are carried out, the desired rhodium compound is precipitated from the solution. The product obtained as a precipitate is separated by filtration and washed several times with a solvent to increase its purity.

In the production of HRh(CO)(SbR$_3$)$_3$ it is desirable to use a starting material in which Z is a bromide or iodide anion. However, even if Z is a chloride anion, Z can readily be converted into a bromide or iodide anion by reaction with potassium bromide or potassium iodide. Thus, the above described seven groups of new rhodium compounds can be obtained in high yield.

The rhodium catalyst used in the present invention may be prepared by synthesizing a rhodium complex represented by the general formula set forth below and combining this complex with excess mixed ligands. For example, the rhodium complex represented by the general formula:

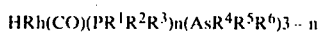

HRh(CO)(PR$^1$R$^2$R$^3$)$_n$(AsR$^4$R$^5$R$^6$)$_{3-n}$ in which R$^1$, R$^2$, R$^3$, R$^4$, R$^5$ and R$^6$ represent alkyl, cycloalkyl, aryl and aralkyl groups and may be same or different, and n is 1 or 2, is made by first contacting RhZ(CO)(PR$^1$R$^2$R$^3$)$_2$ (wherein Z represents a halide anion) with AsR$^4$R$^5$R$^6$ in a solvent, followed by gradually adding a reducing agent of a hydride type of Group IIIA elements of the Periodic Table such as sodium borohydride at a relatively low temperature. Preferably, R$^1$, R$^2$, R$^3$, R$^4$, R$^5$ and R$^6$ are aryl groups and more preferably the same aryl group. In view of the reactivity and commercial availability, it is most preferable that they are all phenyl groups, thus a combination of triphenylarsine and triphenylphosphine. The mixed ligands used in excess may be the same as or different from those contained in the rhodium complex, but the same combinations are advantageous commercially. The ratio of tertiary organo phosphorus to tertiary organo arsenic used as mixed ligands in excess may be chosen within a wide range such that a rhodium complex containing mixed ligands is substantially present. This proportion is generally 20:1 to 1:20, preferably 10:1 to 1:10 and a range of 2:1 to 1:2 is most preferable.

The sum of the amounts of mixed ligands to be added in excess of those capable of combining with a rhodium atom through coordination in a rhodium complex may be chosen within a wide range such that the mixed ligands-containing complex is substantially present. In general, the sum of the amounts of free mixed ligands is 3 mols or more per rhodium atom in the mixed ligands-containing rhodium complex. Since addition of free mixed ligands in too large an excess is disadvantageous with respect to the reaction and cost, the excess amount is preferably 5 to 1000 mols, most preferably 50 to 500 mols per rhodium atom.

As an alternative to using a previously prepared rhodium complex, an oxo catalyst can be formed in situ, i.e. under hydroformylation conditions. That is to say, it is possible to use a method comprising contacting a rhodium metal such as rhodium black or supported rhodium, an inorganic rhodium compound such as rhodium oxide or rhodium nitrate, an organic acid salt such as rhodium acetate or rhodium octoate, or a rhodium complex such as rhodium carbonyl, rhodium dicarbonyl acetylacetone or rhodium carbonyl triphenylphosphine acetylacetone, in the presence of the above described mixed ligands with a mixed gas of carbon monoxide and hydrogen at elevated temperature before or during hydroformylation.

When a hydroformylation reaction of an olefin is carried out using a catalyst according to this invention, the reaction rate is increased to 1.5 to 2 times as much as when a single ligand of tertiary organo phosphorus is used and, accordingly, a reactor can be reduced in size with the same output. Furthermore, it is possible to decrease the quantity of rhodium catalyst to olefin and the concentration of rhodium in a catalyst bed.

The quantity of a rhodium catalyst used in a hydroformylation, depending on the procedure and the variety of olefin used as a starting material, may be chosen—considering these conditions—within a wide range. In a catalyst recycling process wherein an olefin, synthesis gas and rhodium catalyst are fed to a reaction tower, the reaction mixture is withdrawn from the head of the tower, cooled and subjected to reduced pressure to separate a gaseous component, and the liquid product is passed through a distillation column to distill off the product and to give a still residue containing the rhodium catalyst which is then withdrawn from the bottom of the column and recirculated to the reaction tower, for example, the quantity of the rhodium catalyst may be 10 ppm to 5% by weight, preferably 50 ppm to 1% by weight as rhodium metal based on olefin feed. In a liquid fixed bed process wherein an olefin and synthesis gas are fed to a catalyst layer charged previously to a reaction tower and only the reaction product in the form of a mixture of gases and vapors is withdrawn from the top of the tower, the concentration of rhodium in the catalyst layer is generally 10 ppm to 5% by weight, preferably 50 ppm to 1% by weight.

The catalyst system of the present invention may be used batchwise in addition to the continuous procedures described above and is also applicable to liquid, vapor or mixed phase processes. The reaction conditions may be the same as those in the case of using the rhodium-tertiary organo phosphorus type catalysts. That is to say, the reaction temperature is ordinarily room temperature to 150° C., preferably 50° to 130° C., most preferably 80° to 120° C. and the total pressure is ordinarily normal pressure to 100 atmospheres, preferably normal pressure to 50 atmospheres, most preferably 10 to 30 atmospheres. In addition, the hydrogen to carbon monoxide molar ratio is 10/1 to 1/10, preferably 10/1 to 1/1. A solvent is not always indispensable, but in order to maintain stable operation, it is desirable to use a solvent.

The solvent may be chosen from a wide range among those having no detrimental influence on hydroformylation, for example, saturated hydrocarbons such as hexane, decane and dodecane; aromatic hydrocarbons such as benzene, toluene, xylene, cumene and diisopropylbenzene; and oxygen-containing compounds such as alcohols, ketones, esters and preferably products and high boiling point by-products of hydroformylation.

The catalyst system of the present invention can be adapted to α-olefins such as ethylene, propylene, butene-1, hexene-1 and octene-1, olefins with internal double bonds such as butene-2 and octene-2, and vinyl compounds such as styrene, acrylonitrile, acrylic acid esters and allyl alcohols. The present catalyst system is most suitable for obtaining aldehydes rich in normal chain type isomers from α-olefins.

The process for the production of and the identification of the compounds according to the present invention are illustrated in detail in the following examples without limiting the scope of this invention. Examples of the hydroformylation process of this invention are also given.

EXAMPLE 1

Synthesis of Starting Materials (1) Commercially available reagents were used as to rhodium chloride trihydrate $RhCl_3.3H_2O$, triphenylphosphine $PPh_3$, triphenylarsine $AsPh_3$, triphenylstibine $SbPh_3$, sodium borohydride $NaBH_4$ and potassium iodide KI.

(2) Di-μ-chloro-tetracarbonyl dirhodium $(RhCl(CO)_2)_2$ was prepared from $RhCl_3.3H_2O$ and CO by the method disclosed in Inorganic Synthesis, 8, 211 (1966).

(3) Carbonyl bis(triphenylphosphine) rhodium chloride $RhCl(CO)(PPh_3)_2$ was prepared from $RhCl_3.3H_2O$, $PPh_3$ and aqueous solution of formaldehyde by the method disclosed in Inorganic Synthesis, 11, 99 (1968).

(4) Carbonyl bis(triphenylarsine) rhodium chloride $RhCl(CO)(AsPh_3)_2$ and carbonyl bis(triphenylstibine) rhodium chloride $RhCl(CO)(SbPh_3)_2$ were prepared from $[RhCl(CO)_2]_2$ of (2) and $AsPh_3$ or $SbPh_3$ by the method disclosed in Journal of Chemical Society (A), 2287 (1966).

(5) Carbonyl bis(triphenylstibine) rhodium iodide $RhI(CO)(SbPh_3)_2$: 2.0 g (2.29 mmol) of $RhCl(CO)(SbPh_3)_2$ of (4) and 0.42 g (2.53 mmol) of KI were charged in a 200 ml Erlenmeyer flask, to which 150 ml of acetone as a solvent was then added, and the mixture was reacted with agitation at room temperature for 7 hours. Thereafter, the reaction product was filtered, and the product retained on the filter paper was washed three times with acetone and dried under reduced pressure to obtain 1.7 g of the desired, black-brown compound.

Synthesis of New Rhodium Compounds (A) $HRh(CO)(AsPh_3)(PPh_3)_2$ 0.5 g (0.724 mmol) of $RhCl(CO)(PPh_3)_2$ of the foregoing (3) and 0.443 g (1.447 mmol) of $AsPh_3$ were charged to a 300 ml three-necked flask, to which 150 ml of ethanol as a solvent was then added, and the mixture was reacted with agitation at a temperature of 65° C. in a nitrogen stream for 2 hours. Then the flask was immersed in an ice bath to keep the temperature at 0° C. and the mixture was further stirred; to it a solution of 0.5 g (13.21 mmol) of $NaBH_4$ in 50 ml of ethanol was gradually added dropwise over a period of about 30 minutes. Thereafter the flask was withdrawn from the ice bath and the mixture was stirred at room temperature for 2 hours and subjected to filtration in a nitrogen stream. The product retained on the filter paper was washed three times with ethanol and dried under reduced pressure to obtain 0.60 g (0.623 mmol) of a yellow powder (Yield: 86 mol %).

(B) $HRh(CO)(SbPh_3)(PPh_3)_2$

The procedure of the above described (A) was repeated except using 0.511 g (1.447 mmol) of $SbPh_3$ instead of $AsPh_3$ of (A), thus obtaining 0.71 g (0.703 mmol) of a yellow powder (Yield: 97 mol %).

(C) $HRh(CO)(PPh_3)(AsPh_3)_2$

The procedure of the above described (A) was repeated except using 0.5 g (0.642 mmol) of $RhCl(CO)(AsPh_3)_2$ of the foregoing (4) in place of $RhCl(CO)(PPh_3)_2$ of (A) and 0.253 g (0.965 mmol) of $PPh_3$ in place of $AsPh_3$, thus obtaining 0.53 g (0.527 mmol) of a yellow powder (Yield: 82 mol %).

(D) $HRh(CO)(SbPh_3)(AsPh_3)_2$

The procedure of the above described (A) was repeated except using 0.5 g (0.642 mmol) of RhCl(CO)(AsPh$_3$)$_2$ of the foregoing (4) in place of RhCl(CO)(PPh$_3$)$_2$ of (A) and 0.34 g (0.963 mmol) of SbPh$_3$ in place of AsPh$_3$, thus obtaining 0.64 g (0.583 mmol) of a yellow-ochre powder (Yield: 91 mol %).

(E) HRh(CO)(PPh$_3$)(SbPh$_3$)$_2$

The procedure of the above described (A) was repeated except using 0.5 g (0.573 mmol) of RhCl(CO)(SbPh$_3$)$_2$ of the foregoing (4) in place of RhCl(CO)(PPh$_3$)$_2$ of (A) and 0.301 g (1.148 mmol) of PPh$_3$ in place of AsPh$_3$, thus obtaining 0.511 g (0.464 mmol) of a light brown powder (Yield: 81 mol %).

(F) HRh(CO)(AsPh$_3$)(SbPh$_3$)$_2$

The procedure of the above described (A) was repeated except using 0.5 g (0.573 mmol) of RhCl(CO)(SbPh$_3$)$_2$ of the foregoing (4) in place of RhCl(CO)(PPh$_3$)$_2$ of (A) and 0.35 g (1.143 mmol) of AsPh$_3$, thus obtaining 0.40 g (0.350 mmol) of a brown powder (Yield: 61 mol %).

(G) HRh(CO)(SbPh$_3$)$_3$

The procedure of the above described (A) was repeated except using 0.5 g (0.519 mmol) of RhI(CO)(SbPh$_3$)$_2$ of the foregoing (5) in place of RhCl(CO)(PPh$_3$)$_2$ of (A) and 0.367 g (1.039 mmol) of SbPh$_3$ in place of AsPh$_3$, thus obtaining 0.29 g (0.243 mmol) of a black-brown powder (Yield: 47 mol %).

The decomposition temperatures and IR data (infrared spectra) of the componds obtained by the above described procedures (A) to (G) are shown in Table 1, the results of elementary analysis are shown in Table 2 and the relationships between the stretching frequencies of Rh—H and C=O of IR ($\nu_{Rh-H}$ and $\nu_{C=O}$) and the sum of the electronegativities of P, As and Sb in the compounds are shown in FIG. 1 and FIG. 2. As is apparent from these tables and figures, the compounds of the present invention are all single compounds.

TABLE 1

| Rhodium Compound | Color | Decomposition[2] Temperature (°C.) | IR Data[3,4] (cm$^{-1}$) $\nu$Rh-H | $\nu$C=O |
|---|---|---|---|---|
| HRh(CO) (AsPH$_3$) (PPh$_3$)$_2$ | Yellow | 116-118 | 2024(Sh), 2000(S) | 1919(S) |
| HRh(CO) (SbPh$_3$) (PPh$_3$)$_2$ | Yellow | 131-133 | 1994(S) | 1913(S) |
| HRh(CO) (PPh$_3$) (AsPh$_3$)$_2$ | Yellow | 113-115 | 2010(Sh), 1998(S) | 1916(S) |
| HRh(CO) (SbPh$_3$) (AsPh$_3$)$_2$ | Yellow-ochre | 132-134 | 1988(S) | 1897(W) |
| HRh(CO) (PPh$_3$) (SbPh$_3$)$_2$ | Light brown | 126-128 | 1994(S) | 1918(M) |
| HRh(CO) (AsPh$_3$) (SbPh$_3$)$_2$ | Brown | 143-145 | 1985(S) | 1892(W) |
| HRh(CO) (SbPh$_3$)$_3$ | Black-brown | 168-171 | 1982(S) | 1884(W) |
| HRh(CO) (PPh$_3$)$_3$* | Yellow | 137-138 | 2040(S), 2005(S) | 1923(S) |
| HRh(CO) (AsPh$_3$)$_3$* | Yellow | 130-132 | 1992(S) | 1903(S) |

Remarks: * = Known Compound
[2] Decomposition Temperature corresponds to the ordinary melting point since these compounds all melt with decomposition.
[3] IR Data were measured in the form of a tablet with KBr and calibrated by CO.
[4] Letters in parentheses in IR Data show the absorption intensity of peak: (S) = strong; (M) = medium; (W) = weak; (Sh) = shoulder.

TABLE 2

| Rhodium Compound | Found (%) | | | | | | Calculated (%) | | | | | |
|---|---|---|---|---|---|---|---|---|---|---|---|---|
| | C | H | P | As | Sb | Rh | C | H | P | As | Sb | Rh |
| HRh(CO)(AsPh$_3$)(PPh$_3$)$_2$ | 68.61 | 4.92 | 6.29 | 7.88 | — | 10.84 | 68.62 | 4.82 | 6.43 | 7.78 | — | 10.69 |
| HRh(CO)(SbPh$_3$)(PPh$_3$)$_2$ | 65.20 | 4.58 | 6.17 | — | 12.22 | 10.25 | 65.43 | 4.59 | 6.14 | — | 12.06 | 10.19 |
| HRh(CO)(PPh$_3$)(AsPh$_3$)$_2$ | 65.73 | 4.76 | 3.31 | 14.72 | — | 10.33 | 65.62 | 4.61 | 3.08 | 14.88 | — | 10.22 |
| HRh(CO)(SbPh$_3$)(AsPh$_3$)$_2$ | 59.96 | 4.09 | — | 13.80 | 11.37 | 9.52 | 60.19 | 4.23 | — | 13.65 | 11.09 | 9.38 |
| HRh(CO)(PPh$_3$)(SbPh$_3$)$_2$ | 60.07 | 4.25 | 3.00 | — | 21.89 | 9.38 | 60.03 | 4.22 | 2.82 | — | 22.13 | 9.35 |
| HRh(CO)(AsPh$_3$)(SbPh$_3$)$_2$ | 57.52 | 3.94 | — | 6.30 | 21.53 | 9.08 | 57.73 | 4.05 | — | 6.55 | 21.28 | 8.99 |
| HRh(CO)(SbPh$_3$)$_3$ | 55.19 | 3.74 | — | — | 30.57 | 8.88 | 55.46 | 3.89 | — | — | 30.67 | 8.64 |

COMPARATIVE EXAMPLE 1

Using starting materials, solvent and quantity of reducing agent similar to those of Example 1(B), a mixture of RhCl(CO)(PPh$_3$)$_2$ and SbPh$_3$ in ethanol was held at the boiling temperature, to which an ethanol solution of NaBH$_4$ was added dropwise, and the resulting boiling mixture was further stirred for 3 hours. The starting rhodium compound was decomposed and completely dissolved to give a uniform brown solution only. None of the desired compound was obtained.

COMPARATIVE EXAMPLE 2

When the procedure of Comparative Example 1 was repeated except that starting materials, solvent and quantity of reducing agent were similar to those of Example 1(E), the starting rhodium compound was decomposed and none of the desired compound was obtained.

COMPARATIVE EXAMPLE 3

When the same procedure was repeated except that, in place of NaBH$_4$ in Example1(E), an aqueous solution of hydrazine in an equimolar quantity thereto was used, only RhCl(CO)(PPh$_3$)$_2$ was obtained through complete exchange of the ligand.

COMPARATIVE EXAMPLE 4

0.45 g (0.490 mmol) of HRh(CO)(PPh$_3$)$_3$ and 0.173 g (equimolar thereto), 0.346 g (two times mol) or 1.73 g (ten times mol) of SbPh$_3$ were added to 200 ml of ethanol and the resulting mixture was held for 1 hour at the boiling point of ethanol. In each case the starting rhodium compound was only decomposed and none of the compounds aimed at, respectively HRh(CO)(PPh$_3$)$_2$(SbPh$_3$), HRh(CO)(PPh$_3$)(SbPh$_3$)$_2$ and HRh(CO)(SbPh$_3$)$_3$ was obtained.

COMPARATIVE EXAMPLE 5

When the procedure of Comparative Example 4 was repeated except that a temperature of 65° C. was employed instead of the boiling temperature of ethanol and stirring continued for 4 hours, only the starting materials with some decomposed product were recovered, which compositions were not clear, and the desired compounds could not be obtained.

COMPARATIVE EXAMPLE 6

When the procedure of Example 1(G) was repeated except that RhCl(CO)(SbPh$_3$)$_2$ was used instead of RhI(CO)(SbPh$_3$)$_2$, only the starting materials were recovered.

COMPARATIVE EXAMPLE 7

0.130 g (0.498 mmol) of RhCl$_3$.3H$_2$O, 1.054 g. (corresponding to 6 times mol) of SbPh$_3$ and 3 ml of an aqueous solution of formaldehyde were added to 150 ml of ethanol and the mixture was stirred at the boiling temperature of ethanol in a nitrogen atmosphere, to which mixture a solution of 0.188 g (4.95 mmol) of NaBH$_4$ dissolved in ethanol was added dropwise, followed by refluxing for 3 hours. The starting rhodium compound was decomposed but no HRh(CO)(SbPh$_3$)$_3$ product was obtained.

It will clearly be seen from a comparison of Example 1 with the Comparative Examples that the preparation process of the present invention is superior and commercially valuable.

The novel rhodium compounds of the present invention are not only effective as a catalyst for the oxo reaction, but are also usable as a catalyst for the hydrogenation of unsaturated organic compounds, the isomerization of double bonds of olefins, the conversion of hydrogen to deuterium, hydrosilylation, and for various other uses.

The advantages of the compounds of the present invention are illustrated by the use as a catalyst for the oxo reaction with propylene as a raw material, the oxo reaction being carried out by the following procedure.

EXAMPLE 2

20 ml of n-dodecane and 0.109 mmol of a compound of the present invention prepared as described in Example 1 were charged to a 300 ml stainless steel autoclave, which was purged with nitrogen. 5.0 g (119 mmol) of propylene was introduced under pressure into the autoclave which was then heated to 110° C., an H$_2$/CO gas with a molar ratio of 1/1 being introduced, and the reaction was carried out with the reaction pressure maintained at 20 Kg/cm$^2$. The time when the H$_2$/CO gas was no longer absorbed was regarded as the final point of the reaction. After the reaction, the reaction product was subjected to analysis by gas chromatography, giving the results shown in Table 3.

It is apparent from the results of Table 3 that the rhodium compound of the present invention is very effective as a catalyst for the oxo reaction.

TABLE 3

| Rhodium Compound | Reaction Rate $-d(H_2 + CO)/dt$ (ml/sec) | Reaction Time (min) | Conversion of Proplyene (mol %) | Yield of Butylaldehyde (mol %) | n/i Ratio of Butylaldehyde | Yield of Propane (mol %) |
|---|---|---|---|---|---|---|
| HRh(CO) (AsPh$_3$) (PPh$_3$)$_2$ | 13.5 | 13 | 90.8 | 89.8 | 2.0 | 0.7 |
| HRh(CO) (SbPh$_3$) (PPh$_3$)$_2$ | 1.5 | 100 | 43.0 | 42.1 | 1.9 | 0.4 |
| HRh(CO) (PPh$_3$) (AsPh$_3$)$_2$ | 10.2 | 30 | 89.5 | 88.6 | 2.1 | 0.6 |
| HRh(CO) (SbPh$_3$) (AsPh$_3$)$_2$ | 0.5 | 300 | 19.7 | 18.3 | 2.1 | 0.2 |
| HRh(CO) (PPh$_3$) (SbPh$_3$)$_2$ | 1.2 | 275 | 50.4 | 49.8 | 2.0 | 0.4 |
| HRh(CO) (AsPh$_3$) (SbPh$_3$)$_2$ | 0.4 | 300 | 17.7 | 16.8 | 2.2 | 0.3 |
| HRh(CO) (SbPh$_3$)$_3$ | 0.2 | 300 | 7.5 | 7.0 | 2.3 | 0.3 |

EXAMPLE 3

Example 2 was essentially followed with the modification that in addition to 0.109 mmol of the complex HRh(CO)(PPh$_3$)$_2$(AsPh$_3$), triphenylphosphine and triphenylarsine were charged to the autoclave respectively in a proportion of 50 mols to 1 mol of the rhodium complex. The synthesis gas was continuously supplied from a gas holder to keep the reaction pressure constant. After the reaction had been continued for 22 minutes, from the start until the conversion of propylene reached approximately 90%, the autoclave was cooled rapidly and the product was withdrawn and subjected to analysis by gas chromatography. The reaction rate measured by the pressure decrease of the synthesis gas in the gas holder was 8.8 ml/sec. The conversion of propylene was 87.2% and the ratio of normal isomer to branched isomer was 3.7. The quantity of propane formed by the hydrogenation of the propylene was 0.4 mol %.

EXAMPLES 4 TO 9

Hydroformylations using as catalyst the complexes HRh(CO)(PPh$_3$)$_2$(AsPh$_3$) and HRh(CO)(PPh$_3$)(AsPh$_3$)$_2$ prepared in Example 1 were carried out in a manner analogous to Example 3 but with variation of the quantity of excess ligands and reaction conditions, thus obtaining the results shown in Table 4.

COMPARATIVE EXAMPLES 8 TO 12

Hydroformylations using as catalyst the complex HRh(CO)(PPh$_3$)$_3$ synthesized in conventional manner were carried out in a manner analogous to Example 3 with change of conditions as shown in Table 4, thus obtaining the results shown therein.

As can be seen from the Examples and the Comparative Examples, when an oxo reaction is carried out using as catalyst the complex containing mixed ligands and the excess mixed ligands, the reaction rate is increased to about 1.5 to 2 times as much as that obtained when using the complex containing phosphine only and the excess phosphine only, the normal chain to branched chain ratio of butylaldehyde is somewhat increased and the quantity of propane formed is somewhat decreased.

EXAMPLE 10

The hydroformylation reaction described in Example 3 was essentially repeated except that there was used as catalyst a still residue containing the rhodium catalyst and excess mixed ligands obtained by distilling the product of the hydroformylation reaction of Example 4 and separating the aldehyde. The results obtained are shown in Table 4, from which it is apparent that the activity and selectivity are not changed and thus the catalyst can be reused even after a heat treatment such as distillation.

EXAMPLE 11

The hydroformylation of Example 4 was repeated except that there was used a catalyst consisting of rhodium supported on activated carbon (Rh content: 1.0% by weight) and excess mixed ligands, thus obtaining the results shown in Table 4.

TABLE 4

| Ex. No. | Rhodium Complex (0.109 mmol) | $PPh_3/Rh$ Complex (mol ratio) | $AsPh_3/Rh$ Complex (mol ratio) | Reaction Temperature (°C.) | $H_2/CO$ (mol ratio) | Reaction Rate $-d(H_2/CO)dt$ (ml/sec) | Propylene Conversion (mol %) | Butylaldehyde Normal/Branched Ratio | Propane Yield (mol %) |
|---|---|---|---|---|---|---|---|---|---|
| 3 | $HRh(CO)(PPh_3)_2(AsPh_3)$ | 50 | 50 | 110 | 1.0 | 8.8 | 87.2 | 3.7 | 0.4 |
| 4 | " | 67 | 33 | 110 | 1.0 | 7.0 | 89.3 | 3.9 | 0.2 |
| 5 | " | 100 | 50 | 110 | 1.0 | 6.0 | 89.1 | 4.5 | 0.3 |
| 6 | " | 67 | 33 | 90 | 1.0 | 1.8 | 87.5 | 3.9 | 0.2 |
| 7 | " | 100 | 50 | 110 | 5.0 | 7.6 | 88.1 | 8.2 | 1.8 |
| 8 | " | 67 | 33 | 110 | 5.0 | 9.1 | 92.9 | 6.4 | 1.6 |
| 9 | $HRh(CO)(PPh_3)(AsPh_3)_2$ | 33 | 67 | 110 | 1.0 | 12.6 | 88.7 | 3.5 | 0.4 |
| 8* | $HRh(CO)(PPh_3)_3$ | 67 | 0 | 110 | 1.0 | 4.4 | 86.4 | 3.4 | 0.3 |
| 9* | " | 100 | 0 | 110 | 1.0 | 4.0 | 90.2 | 4.0 | 0.7 |
| 10* | " | 100 | 0 | 110 | 5.0 | 5.5 | 90.5 | 6.6 | 2.8 |
| 11* | " | 33 | 0 | 110 | 1.0 | 5.8 | 89.5 | 2.7 | 0.6 |
| 12* | " | 100 | 0 | 90 | 1.0 | 1.0 | 87.2 | 4.0 | 0.4 |
| 10 | Catalyst of Ex.4(reused) | — | — | 110 | 1.0 | 6.8 | 90.2 | 3.9 | 0.2 |
| 11 | Rh/C (Rh 1.0 wt. %) | 67 | 33 | 110 | 1.0 | 6.0 | 88.2 | 3.8 | 0.2 |

Note:
Total pressure = 20 Kg/cm²
* = Comparative Example

What is claimed is:

1. A process for the hydroformylation of olefins by the reaction of an olefin with carbon monoxide and hydrogen to produce an aldehyde having one more carbon atom than the olefin wherein there is used as catalyst at temperatures in the range of ambient to about 150° C., a total pressure in the range of atmospheric to about 100 atmospheres and a $H_2/CO$ mol ratio of 10/1 to 1/10, a preformed rhodium complex having the general formula

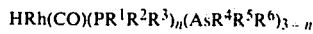

in which $R^1, R^2, R^3, R^4, R^5$ and $R^6$ are selected from the group consisting of alkyl, cycloalkyl, aryl and aralkyl and may be the same or different and n is 1 or 2, in the presence of excess mixed ligands of P and As having substituents selected from said group which may be the same as or different from those contained in the rhodium complex.

2. A process according to claim 1 in which a solvent is present selected from the group consisting of saturated hydrocarbons, aromatic hydrocarbons, oxygen-containing compounds and hydroformylation products and byproducts.

3. A process according to claim 1 in which $R^1$, $R^2$, $R^3$, $R^4$, $R^5$ and $R^6$ are single ring aryl groups.

4. A process for the hydroformylation of olefins by the reaction of an olefin with carbon monoxide and hydrogen to produce an aldehyde having one more carbon atom than the olefin wherein there is used as catalyst at temperatures in the range of ambient to about 150° C., a total pressure in the range of atmospheric to about 100 atmospheres and a $H_2/CO$ mol ratio of 10/1 to 1/10, a preformed rhodium complex having the formula

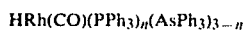

in which n is 1 or 2, in the presence of excess mixed ligands of $PPh_3$ and $AsPh_3$.

5. A process according to claim 4 in which the olefins have 2-8 carbon atoms.